_United States Patent_ [19]

Dawson et al.

[11] Patent Number: 4,578,515

[45] Date of Patent: Mar. 25, 1986

[54] PREPARING N-VINYLFORMAMIDE

[75] Inventors: Daniel J. Dawson, Los Altos; Kenneth M. Otteson, Redwood City, both of Calif.

[73] Assignee: Air Products and Chemicals, Inc., Allentown, Pa.

[21] Appl. No.: 618,420

[22] Filed: Jun. 7, 1984

Related U.S. Application Data

[62] Division of Ser. No. 318,615, Nov. 5, 1981, Pat. No. 4,490,557.

[51] Int. Cl.$^4$ ........................................ C07C 103/127
[52] U.S. Cl. ........................ 564/215; 525/355; 525/369; 525/371; 525/375; 525/377; 526/75; 526/307.1; 564/159; 564/160
[58] Field of Search ................... 564/215, 159, 160

[56] References Cited

U.S. PATENT DOCUMENTS 4,490,557 12/1984 Dawson et al. ............... 564/159

_Primary Examiner_—Robert V. Hines
_Attorney, Agent, or Firm_—Russell L. Brewer; E. Eugene Innis; James C. Simmons

[57] ABSTRACT

Ethylidene bisformamide is prepared by reacting, at elevated temperatures, dry acetaldehyde and formamide in the presence of an acidic catalyst and an ammonia scavenger such as acetic anhydride. The bisformamide is recovered as a bottoms product of high speed low residence time distillation techniques, e.g., wiped film evaporation. The resulting ethylidene bisformamide may be cracked to N-vinylformamide, which monomer is useful in the preparation of active polymers and copolymers, including poly(vinylformamide) which can be hydrolyzed to poly(vinylamine) salts by contact with acid. These amine salts can then be converted to the free amines, which are precursors of polymeric dyes and pharmaceuticals.

3 Claims, 3 Drawing Figures

PREPARING N-VINYLFORMAMIDE

This application is a division of application Ser. No. 318,615 filed Nov. 5, 1981 and now U.S. Pat. No. 4,490,557.

BACKGROUND OF THE INVENTION

1. Field of the Invention

The invention is in the field of preparing ethylidene bisformamide from acetaldehyde and formamide, and, optionally thereafter, cracking (thermally decomposing) the ethylidene bisformamide to N-vinylformamide. This invention also relates to a chemical process for forming poly(vinylamine) salts of mineral acids, especially poly(vinylamine hydrochloride) from the resulting N-vinylformamide.

2. Description of the Prior Art

Poly(vinylamine), its salts, and products based thereon are desirable chemicals. Efficient and effective integrated overall processes for the production of poly(vinylamine) salts and poly(vinylamine) itself, of course, would encourage and promote the widespread commercial use of said chemicals. U.S. Pat. No. 4,018,826, issued on Apr. 19, 1977, to Richard Gless, Daniel J. Dawson, and Robert E. Wingard, discloses a process for preparing poly(vinylamine) wherein acetaldehyde and acetamide are formed into ethylidene-bisacetamide which is then cracked to yield vinylacetamide which is polymerized and hydrolyzed to poly(vinylamine). In said patent, acetaldehyde and acetamide are reacted in a liquid phase in the presence of an aqueous strong liquid mineral acid.

In U.S. Pat. No. 4,176,136, issued on Nov. 27, 1979 to Daniel J. Brenzel, an improved method for carrying out this reaction is disclosed wherein ethylidene-bisacetamide is prepared by the process of contacting a liquid mixture of acetaldehyde and acetamide with a solid cation exchange resin at a temperature of from about 10° C. to about 110° C.

Other references to the condensation reaction of acetaldehyde and acetamide in the prior art include V. V. Richter, Ber. 5,477(1877); W. Noyes et al, *J. Am. Chem. Soc.*, 55,3493 (1933) and Ben Ishai et al, *Tetrahedron Letters*, 50,4523 (1965). Also, a general review article on the condensation of aldehydes and amines may be found in *Organic Reactions*, 14,52 (1965).

An effective and efficient process for producing poly(vinylamine) salts in good yields beginning with formamide, however, has heretofore not been known. Indeed, the sole references known to us regarding even the preparation ethylidene bisformamide, Keimmel, et al; *J. Org. Chem.*, 36, 350 (1971), and Takase, et al, *Sci.-Rep.* (Osaka), 16(1), 7 (1967) shows very mediocre yields. Similarly, when acetamide is merely replaced by formamide in the Gless et al or Brenzel processes, a usable product is not obtained. Rather, a low yield dark-colored degraded product is generally the result.

It is an object of the instant invention to provide an effective process for producing ethylidene bisformamide from formamide and acetaldehyde.

SUMMARY OF THE INVENTION

We have now found that ethylidene bisformamide can be formed in high yields from formamide and acetaldehyde provided that the following precautions, to our knowledge previously neither known nor disclosed to be important, are observed. First, the reaction must be carried out at an elevated temperature that is generally above the temperature achieved by the reaction's exotherm on a laboratory scale. Second, the reaction must be scrupulously freed of ammonia which is present as a contaminant in the formamide feed and tends to be generated during the condensation reaction as well. Two other factors which enhance yield are minimizing water in the reaction zone and employing a low residence time means such as a film evaporator to isolate the ethylidene bisformamide as a bottoms. It is an aspect of this invention to prepare and recover ethylidene bisformamide by a process incorporating these precautions.

Further aspects of this invention involve the use of this improved process in combination with further steps to provide intermediate polymers and ultimately poly(vinylamine) and polymer products based thereon.

BRIEF DESCRIPTION OF THE DRAWINGS

In the DETAILED DESCRIPTION OF THE INVENTION, reference will be made to the drawings in which.

DETAILED DESCRIPTION OF THE INVENTION

Figure 1:
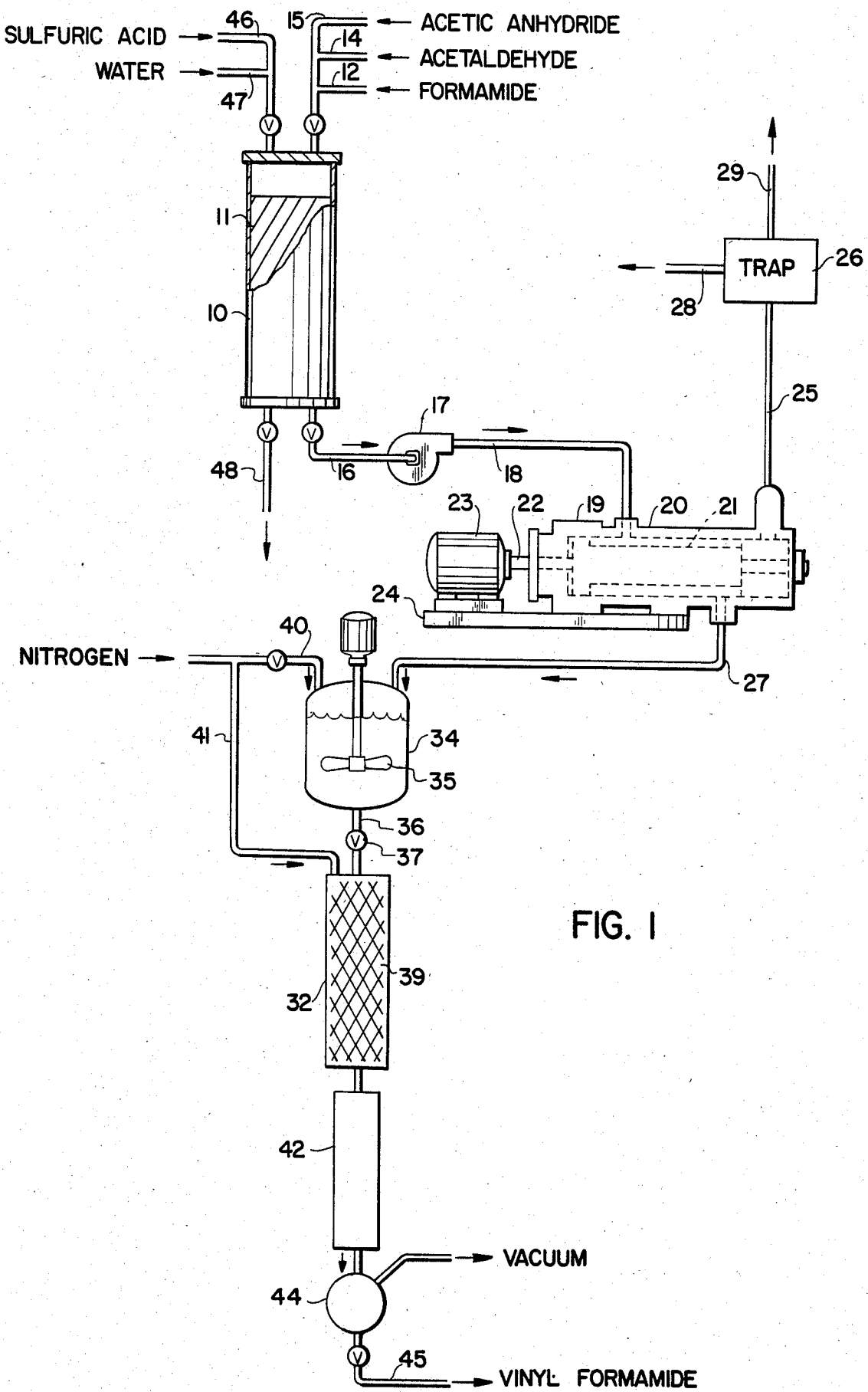
FIG. 1 illustrates a continuous embodiment of the instant invention wherein ethylidene bisformamide is produced in the presence of an ion exchange resin catalyst, recovered using a wiped film evaporator and pyrolyzed to give N-vinylformamide.

Fundamentally, this process for preparing ethylidene bisformamide proceeds via the condensation reaction of formamide and acetaldehyde shown in General Formula I.

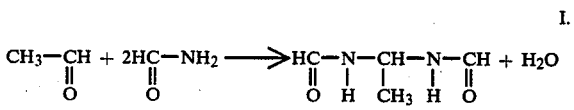

This reaction is carried out in the presence of an acid catalyst.

The invention concerns factors that must be controlled to achieve acceptable yields of ethylidene bisformamide from this reaction. Two major factors that must be controlled are:

Scrupulous minimization of free ammonia in the reaction feeds, reaction zone, and reaction products and Use of elevated reaction temperatures.

Two other factors that advantageously are controlled are:

Minimization of water in the reaction zone and

Use of a low resistance time distillation means, such as a film evaporator to remove light impurities, unreacted feedstocks and the like to give the "bis" product as bottoms.

AMMONIA CONTROL

Formamide is an inherent source of ammonia contamination. It almost always contains ammonia or degrades to give minor amounts of ammonia. In the present reaction, ammonia can be generated as a side product. We have found that this ammonia leads to side reactions, major yield losses and gross product discoloration. Accordingly, it is necessary to minimize ammonia build-up. This is done by adding an ammonia scavenger, a compound that will consume a base like ammonia. Such scavengers include acetic anhydride, acetic-formic anhydride or an acidic ion exchange resin or the like that will absorb any ammonia that may be present. Acetic anhydride is quite effective, while solid ion exchange resins offer the advantage of being easily separated from the reaction mixture. The ion exchange resin employed in general is the same type of acidic resin that can be employed as catalyst for the desired condensation reaction and that will be discussed in more detail in that context. Combinations of acetic anhydride and resin can be employed, as well.

The amount of acetic anhydride is generally from about 0.003 to 0.500 equivalents (based on the formamide present) with amounts from 0.005 to 0.100 equivalents being preferred. Larger amounts may be employed but are seen to possibly offer cost and purification disadvantages not clearly offset by superior yields, etc.

TEMPERATURE CONTROL

The reaction must be carried out at moderately elevated temperatures. The reaction is exothermic so that, on a laboratory scale, room temperature feedstocks can result in a reaction zone temperature of from about 25° to about 50° C. This temperature is too low. Higher temperatures, such as from 50° to 100° C. or higher, must be employed. Preferred temperatures are from 50° C. to 90° C. with 50° C. to 80° C. being the most preferred temperature range.

WATER CONTROL

It is advantageous to minimize water in the reaction zone. This can be accomplished by drying feedstocks and the catalyst employed. Water is generated in the desired reaction and can in part be trapped by acetic anhydride if present. Other steps to minimize water include blanketing the reaction zone with a dry gas and the like.

HIGH SPEED DISTILLATION

Following the reaction, the acidic catalyst for the condensation is removed from the ethylidene bisformamide reaction product. If the catalyst employed is a liquid acid, it can be eliminated either by physical removal or by reaction with a neutralizing amount of an acid acceptor. Suitable acid acceptors include alkali metal and alkaline earth metal hydroxides, carbonates, bicarbonates and oxides. Satisfactory results can be obtained with any of these materials, so cost factors dictate a preferance for sodium, potassium and calcium hydroxides, carbonates, bicarbonates and oxides. The carbonates are most preferred if the reaction product is to be thermally decomposed (cracked) to N-vinylformamide since that reaction should be carried out under nonacidic conditions and carbonates provide a buffering action at or about the desired neutral pH's. If the condensation catalyst was an ion exchange resin, as is preferred, the catalyst removal is simply effected since the resin is solid and the reaction product is liquid. For example, in a continuous reaction mode, the reaction product can be drawn off through a filter, settling basin or a like solid-liquid separation means. When employing a batch mode, a similar solid-liquid separation step can be employed to effect isolation of the crude reaction product from the solid resin.

The catalyst-free crude reaction product generally contains ethylidene bisformamide, water, acetic acid and unreacted formamide and acetaldehyde as its principal components. It also likely contains minor amounts of byproducts.

In recovering the ethylidene bisformamide from this reaction product, it is preferred that the recovery be conducted under high speed-low residence time conditions in order to obtain a usable product. It has been found that conventional column vacuum distillation techniques wherein the impurities, i.e., formamide, acetaldehyde, acetic acid and water, all being more volatile than ethylidene bisformamide, are distilled overhead result in poor product quality and large yield losses. Thus, for acceptable results this recovery comprises treating the crude reaction product in a "thin film" configuration rather than in a "bulk" form, with exposure to a relatively high temperature being maintained for a relatively brief time.

The exposure to heat takes place under volatilizing conditions and high surface area conditions, which allows for the high speed-low residence time of the recovery process. The exposure temperature is suitably in the range of from about 150° C. to about 350° C., with temperatures in the range of from about 160° C. to about 300° C. being preferred. These temperatures are wall temperatures, with the actual temperature of the ethylidene bisformamide being somewhat lower as a result of cooling caused by the evaporation of the water and unreacted reagents.

A vacuum is employed and will generally fall in the range of from about 1.0 mm Hg absolute to about 100 mm Hg absolute. Absolute pressures below 1.0 mm are very satisfactory as well but are difficult to achieve in commercial scale equipment with substantial reactant and water partial pressures being exhibited. Pressures above 100 mm Hg should generally be avoided as it is difficult to obtain desired removal of contaminants at higher pressures without resorting to detrimentally high temperatures or detrimentally long residence times. Preferred absolute pressures are in the range of from about 1.0 mm Hg to about 35 mm Hg with 2.0 mm Hg to 30 mm Hg being a most preferred range.

The time during which the ethylidene bisformamide is exposed to high temperature should be limited as much as possible. Generally, times at temperature of from about a second or so to a minute or two are acceptable, with times from 1 second to 30 seconds and especially 1.0 to 20 seconds being preferred. It is to be understood, of course, that in the case of continuous processing these times would be mean times.

The bisformamide is treated in a "thin film" form and during treatment should have a surface area of at least 4 $cm^2$/gram, and preferably of at least 6 $cm^2$/gram and more preferably of at least 8 $cm^2$/gram. To obtain reasonable processing rates, it is generally desirable to limit surface area to a maximum of about 50 $cm^2$/gram. These conditions can be attained in "thin film" evaporators such as horizontal or vertical wiped film evaporators, multiple screw extruder evaporators, or the like. Falling film evaporators can also be employed but care must be taken to avoid scorching which can develop if the resulting film is not sufficiently uniform.

Of these types of evaporating apparatus, those such as wiped film evaporators which cause the bisformamide to be agitated during recovery are preferred.

The product of this distillation generally is relatively pure ethylidene bisformamide.

OTHER CONDENSATION REACTION CONDITIONS

As can be seen in General Formula I, above, stoichiometrically, acetaldehyde and formamide react in a molar ratio of 1:2. Generally, however, it is preferred to use somewhat of an excess of formamide. Major excesses do not appear to offer any benefit, so suitably the ratio is controlled from 1:2 to about 1:6 inclusive, with ratios of from about 1:2 to 1:3 being most preferred. Reaction will occur at ratios outside these ranges, such as below 1:2 or above 1:6, but such conditions are not seen to offer any advantage and present the obvious disadvantage of involving a large excess of one reactant or the other which must be recovered and recycled.

The condensation reaction is conducted in the presence of a catalytic amount of an acidic catalyst, selected from among lower alkanoic acids (formic or acetic), mineral acids, or acidic ion exchange resins. Good results are obtained when a mineral acid, such as sulfuric or hydrochloric acid, or formic or acetic acid is added in a catalytically effective amount such as from about 0.001 to 1 mole of acid per mole of formamide. More preferred is from 0.002 to 0.1 mole of acid per mole of formamide. As previously noted, water addition with such catalysts should be minimized.

When an ion exchange resin is employed in the present process it is preferably solid and insoluble in the reaction medium, the reactants and the products. It is a cation exchange resin.

Cation exchange resins contain acidic groups such as carboxylic acid and sulfonic acid groups or radicals. They are not, however, necessarily acidic in the sense of giving a pH value of less than 7 to water in contact therewith. Examples of suitable resins include resins derived from monohydric and polyhydric phenols and aldehydes which are further modified by reaction with sulfurous acid, sulfites and sulfur dioxide and sulfonated polystyrene which is crosslinked such as with divinylbenzene. Examples of such materials are those which are available commercially from Dow Chemical Company under trademarks such as Dowex 50W-X8, 10, 12 and 16 and Dowex MSC-1; from Rohm and Hass Company under the trademarks Amberlite 200, Amberlite IR 118, 120, 122 and Amberlite IRC 50; from Diamond Shamrock as Duolite C-3, C-20, C-20X10, CC-33 and C-25D; from Permutit Company (England) as Zeocarb 225, 215 and 266; from Permutit Company (USA) as Permutit Q, Q 110, and Q 210; and from Bio-Rad Laboratories as BioRex 40 and 70 and as AG-50-X8 and AG-MP-50. Other comparable commercial or prepared ion exchange resins can be used, as well as can mixtures of two or more resins.

Preferred because of ready availability, are the sulfonated divinylbenzene-crosslinked polystyrenes such as Amberlite IR-120 and AG-MP-50. The resins should be employed in a protonated state, that is in their H+ forms. This form is obtained by contacting the resin with aqueous mineral acid, such as aqueous $H_2SO_4$, HCl, HBr, $HNO_3$ or the like, prior to use. This acid treatment can also serve to regenerate an ion exchange resin which has become deactivated. This deactivation can occur when ammonia and ammonium ions present in the formamide-acetaldehyde feed displace the hydrogen ions on the resin. The acid treatment may be carried out at a temperature of 10° to about 100° C. and, preferably from 20° C. to about 50° C., and for a time of about 10 minutes to about 24 hours, and preferably 1 hour to about 4 hours. The acid is generally dilute, with concentrations of from 0.1 to 6 molar in water being preferred, with at least one mole of acid per mole of protonated sites desired being employed. Following the acid treatment, the resin may suitably be rinsed with water to remove residual acid and dried.

An additional resin treatment also is advantageous. Immediately prior to use, the resin is washed with a mixture of acetic anhydride and formamide and dried. When this is done, the necessity of adding acetic anhydride to the reaction mixture lessens. A suitable catalyst rinse for a kg of resin would be a kg or two of formamide containing 5 to 20% acetic anhydride.

The contacting of the reactants with the catalyst, e.g., ion exchange resin, or acid catalyst, with or without acetic anhydride may be carried out in a continuous or a batch mode. In the continuous mode, the reactants are generally fed in the desired ratio to a reaction zone containing the catalyst, preferably an ion exchange resin. The resin may be in a fixed bed, stirred or fluidized bed configuration. The reaction products are continuously withdrawn from the reaction zone. The rate at which the reactants are fed to the reaction zone is expressed in terms of the weight hourly space velocity (WHSV) of acetaldehyde passed over or contacted with the ion exchange resin in $$\frac{\text{Kg of acetaldehyde}}{\text{Kg of ion exchange resin} \times \text{hour}}$$

WHSVs of from 0.01 to 2 kg/kg×hour are usefully employed with WHSVs of from 0.05 to 1 kg/kg×hour being preferred.

In a batch mode, it is suitable to react from about 0.01 to about 10 kg of acetaldehyde per kg of resin and to employ reaction times of from about 0.25 hour to about 24 hours. Preferably about 0.05 to about 1 kg of acetaldehyde are used per kg of resin with times of from about 0.5 hours to about 24 hours. Most preferred batch conditions include 0.1 to 1.0 kg of acetaldehyde per kg of resin and a time of 1 hour to 6 hours. In either the batch or the continuous mode, the catalyst resin is usually employed in particulate form.

CRACKING OF THE ETHYLIDENE BISFORMAMIDE

Ethylidene bisformamide product of the aforediscussed process, can be thermally decomposed (cracked) to N-vinylformamide in accord with General Formula II II.
HC—N—CH—N—CH $\xrightarrow{\text{Heat}}$
‖   |   |   |   ‖
O   H   CH$_3$   H   O

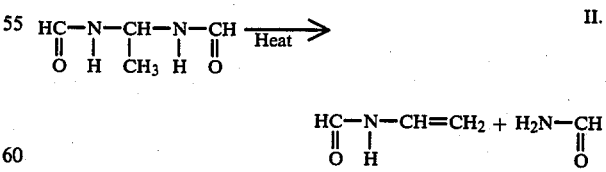

This cracking is carried out by heating the ethylidene bisformamide to a temperature in the range of from about 150° C. to 750° C. preferably 300° C.–625° C. for from about 0.1 seconds to about 1 hour, more preferably for from 0.2 seconds to 2 minutes in the presence of a solid surface catalyst. Suitable catalysts include solid inorganic materials, preferably of a siliceous, carbonate or oxidic nature. As a general rule, catalysts that are not strongly acidic give best results. (A useful catalyst is one which by art-known tests, such as Hammett indicators, does not give a strongly acidic reading.) Typical useful catalysts include siliceous catalysts such as diatomaceous earth, fumed silica, chopped glass fiber, powdered or formed glass, silica gel, and fine sand; and inorganic carbonate minerals such as marble or other forms of calcium carbonate. Inert solid metals such as steel and stainless steel may be used as well. Strongly acidic materials to be avoided include silica-alumina hydrocarbon cracking catalysts and the like. With carbonate catalysts, such as marble, somewhat lower temperatures, say 300°–425°, are effective. With other of these nonacidic materials that exact nature and form of the catalyst is not critical as these other materials may largely serve as heat transfer media.

These catalysts can be employed in low surface area forms such as in the form of glass chips, marble chips, and the like. They may also be in high surface area forms having areas of at least about 1 m²/g, such as with surface areas of from about 10 m²/g to about 400 m²/g. They may be added to the reaction mixture as powders, pellets or the like or can be employed as a bed through which the reaction mixture is passed. The area or form of the catalysts is not seen to be critical to their use in this reaction. Preferred catalysts include glass chips or the like and marble chips having a 0.01 to 1.0 m²/g surface area and diatomaceous earth "Celite" having a 0.1 to 5 m²/g area. Suitable reaction times for the catalytic cracking step are from 0.01 minute to about 1 hour, preferably 0.03 minutes to 0.25 hours.

The N-vinylformamide which is formed in this reaction step is more volatile than the ethylidene bisformamide feed material. It is desirable to remove it by volatilization from the pyrolysis reaction zone as it is formed. This may be done by pulling a vacuum on the reaction zone during reaction. Vacuums of from about 10 mm Hg to about 100 mm Hg are suitable to effect volatilization of the N-vinylformamide at the cracking reaction temperatures. Residual formamide volatilized along with the N-vinylformamide may be removed, if desired from the N-vinylformamide. This treatment may take the form of fractional crystallization, distillation, or the like.

POLYMERIZATION OF N-VINYLFORMAMIDE

The N-vinylformamide monomer, with or without purification treatment, can be polymerized or copolymerized. This polymerization can be carried out in a liquid reaction medium using a free-radical initiator catalyst. There are two classes of suitable liquid media. Polar hydrogen-bonding liquids, like water and lower alkanols, are suitable and function as solvents for the monomer and the polymer product. Nonpolar liquids, such as hydrocarbons, ethers, and ketones, are also suitable, functioning as monomer solvents but not as solvents for the polymer, the polymer thereby forming a second phase. Lower alkanols of from one to five carbons such as methanol, isopropanol, n-butanol and the like, are preferred media, with isopropanol being most preferred.

The amount of reaction media is generally selected to provide a concentration of monomer of from about 10% to 50% by weight. Lower concentrations could be employed, but are not seen to offer any significant advantage.

N-vinylformamide can be formed into homopolymers or it can be formed into copolymers with other free-radical polymerizable monomers. These other monomers can be selected from among other vinyl group containing compounds such as vinyl chloride, vinyl acetate, vinyl sulfonate, acrylic acid, acrylic acid esters, styrene, divinylbenzene, and the like. Other comonomers such as ethylene, propylene, butadiene, vinyl ethers, maleic anhydride, acrylamide, and N-vinylacetamide can be added as well. The comonomers may be added eight to "dilute" the N-vinylformamide functionality and likely give a lower priced product or to impart a new or different functionality. Certainly, the above list of possible monomers is not to be construed as limiting and other compounds known to the art as comonomers in "vinyl"-type polymers may be employed.

A free-radical initiator is required to catalyze the polymerization. Suitable catalysts include the organic peroxides such as dicumylperoxide and other materials known in the art for this purpose. A commonly available catalyst is AIBN, 2,2,-azobis-(2-methylpropionitrile). The amount of catalyst is not critical. Generally, amounts of from about 0.1 gram to about 20 grams of catalyst per 100 grams of vinyl monomer are employed with additions of from 0.1 to 2 grams of catalyst per 100 grams of vinyl monomer being preferred.

The polymerization is generally carried out at a moderately elevated temperature such as from about 25° C. to about 125° C., with temperatures of from about 50° C. to about 110° C. being preferred. The polymerization requires from about 1 to 8 hours for completion, depending upon the exact temperature, catalyst, and monomer concentration employed. Generally, the reaction will be monitored by NMR or gas chromatography for unreacted monomer and continued until no significant monomer remains, for example, less than 5%, preferably less than 1%. The reaction medium is then removed and the polymer is recovered by precipitation in a nonsolvent. Typical nonsolvents include nonpolar organic liquids such as ketones, ethers and hydrocarbons, for example acetone, methyl ethyl ketone, methyl isobutyl ketone, diethyl ether, diisopropyl ether, hexane, cyclohexanol, n-pentane, benzene, and the like.

Following precipitation, the polymer product which is represented by general Formula III is recovered and optionally washed and/or dried.

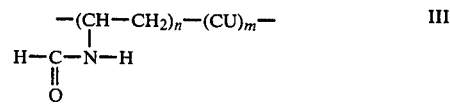

wherein CU is the optional copolymeric unit, n is a positive integer and m is 0 or a positive integer.

HYDROLYSIS

The N-vinylformamide polymers or copolymers so formed are often hydrolyzed to polymeric amines.

This hydrolysis is suitably carried out in water in the presence of a strong acid. At least one equivalent of acid per equivalent of poly(vinylformamide) should be used, such as from 1.05 to 3 equivalents of acid per equivalent of polymer. Too great an excess of acid can cause the hydrolysis product to precipitate prematurely. Suitable acids include, for example, hydrochloric, sulfuric, p-toluene sulfonic, trifluoroacetic, perchloric and hydrobromic acids, with hydrochloric acid being preferred.

This hydrolysis is carried out at elevated temperatures such as at the reflux temperature of the solution (about 110° C.) or temperatures in the range of from about 60° C. to 175° C. and, depending upon the temperature, requires from about 1 hour to about 36 hours, preferably 3 hours to 12 hours, to complete.

Following hydrolysis, the polymer salt can be recovered by further acidifying to cause it to precipitate. This may be carried out by adding additional acid to a concentration of 1 to 3N, cooling, and isolating the precipitating polymer. The precipitated polymer initially is a gum, but, upon drying, forms a granular solid of poly(vinylamine) salt, such as the hydrochloride or the like. This product is a linear repeating polymer of the formula

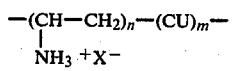

wherein CU is the optional copolymeric unit(s), n is 25 to 10,000 and m is 0 to 10,000 so as to provide a molecular weight of from about 4,000 to 800,000 and $X^-$ is the anion corresponding to the acid employed in the hydrolysis.

The process may be halted at this point, yielding as its product a poly(vinylamine) salt. It also may be carried further, such as to form the free amine. This conversion may be effected by contacting the salt with an aqueous base such as an alkali metal or alkaline earth metal oxide or hydroxide, at a pH of 10 or greater. Typical useful bases include sodium hydroxide and potassium hydroxide. Other basic materials may be used as well, but are not as advantageous costwise. This neutralization may be carried out at temperatures in the range of 15°–50° C., such as at room temperature. This yields the polymeric free amine which may be isolated and dried, if desired. The polyvinyl amine product is a linear polymer. It is water-soluble and has a formula

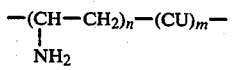

wherein n and m have values as above described such that the polymer has a molecular weight of from about 2,000 to about 450,000.

One excellent use of the polymeric amine is in the manufacture of polymeric azo and non-azo colorants with the amine functionalities being useful for attaching the chromophoric groups to the polymer backbone. This use is fully described in U.S. Pat. Nos. 4,018,826 and Re. 30,362 of Gless et al; 4,051,138 of Wingard et al, 4,107,336 of Otteson et al or 4,182,885 of Bunes. It may also be used as a water clarification aid as shown in U.S Pat. No. 4,217,214 of Dubin or as a polymeric drug backbone as shown in U.S. Pat. No. 4,190,716 of Parkinson et al. All these patents are herein expressly incorporated by reference.

The invention will be further described with reference to the accompanying drawings.

Referring to FIG. 1, ethylidene bisformamide is produced in the presence of an ion exchange resin catalyst and acetic anhydride. Elongated cylindrical reactor 10 is charged with a bed 11 of particulate sulfonated divinylbenzene-cross-linked polystyrene ion exchange resin previously rinsed with formamide containing 10% acetic anhydride and thereafter together with the reaction zone, dried. This resin is in the protonated ($H^+$) form. Dried formamide, acetaldehyde and acetic anhydride, in a 3:1:0.2 mole ratio, are continuously fed to the top of the resin bed via valved conduits 12, 14 and 15, respectively. The rate of reactant feed is regulated to provide a WHSV of from 0.01 to 2 kg of acetaldehyde/kg of resin/hour. Heat can be added to or removed from reactor 10 by means not shown as needed to control the reaction temperature above 50° C. A crude reaction product composed principally of water, unreacted, acetaldehyde and formamide, acetic acid and ethylidene bisformamide is continuously removed via valved conduit 16 to metering pump 17 by which it is fed via conduit 18 to wiped film evaporator 19. Optionally, the crude reaction product drawn off can be first passed through a filter or the like.

The evaporator 19, which can be any suitable high speed-low residence time (high surface area) film evaporator, in the Fig. comprises an outer housing 20, internal rotating wiper blade 21 driven by shaft 22 and motor 23, and a base 24. Outer housing 20 is maintained at a temperature of 180°–270° C. A vacuum of less than 50 mm Hg absolute is pulled on evaporator 19 via conduit 25. As the reaction product mixture is fed into the evaporator it is spread on the inside of heated housing 20 by rotating wiper blade 21. The feed rate is controlled to give a mean residence time in the evaporator of about only 2–30 seconds. The clearance between blade 21 and housing 20 is such that the surface area of the liquid is about 10–15 cm²/gm.

As liquid is fed, it moves from the feed end of evaporator 19 to the product end. The ethylidene bisformamide product is withdrawn from the evaporator as a liquid via conduit 27. The water, unreacted reactants, by-products and acetic acid are taken off as vapors via conduit 25 to a trap 26 where condensation takes place. The condensed materials are removed via conduit 28 and the remaining volatiles are removed via conduit 29. The formamide and other unreacted feeds are preferably recovered and recycled to the feed conduits following condensation by means not shown.

The ethylidene bisformamide, in order to form N-vinylformamide, can then be passed via line 27 to cracker 32. Cracker 32 is made up of feed vessel 34 equipped with agitator 35 and heating means (not shown) to prevent solidification of the bisformamide feed. The bisformamide is passed through line 36 at a rate controlled by valve 37 to pyrolysis column 39 which is heated by means not shown to 200°–250° C. in a top evaporator stage followed by 550° C. in a lower pyrolysis section that contains a bed of pyrolysis catalyst. Pyrolysis column 39 is at an absolute pressure of from 10 to 100 mmHg with a stream of nitrogen provided via lines 40 and 41 carrying the volatile pyrolysis products down from column 39 to condenser 42 where the N-vinylformamide liquifies and is collected in chilled receiver 44. A vacuum is pulled on receiver 44 to remove volatile contaminants. The N-vinylformamide product is removed via line 45.

As the continuous process shown in FIG. 1 is run, the resin bed 11 gradually becomes contaminated and deactivated by ammonia and ammonium salts which are normally present in the formamide feed. Periodically, feed conduits 12, 14 and 15 are blocked off. The valve on product conduit 16 is closed and an aqueous mixture of acid and water, such as sulfuric acid, is charged to the reactor via lines 46 and 47, respectively. This removes the deactivating salts and returns the resin bed to activity. The acid-water mixture is removed via conduit 48 and the bed is rinsed with water via conduit 47 which rinse is also removed via conduit 48. Thereafter, the bed is optionally rinsed with formamide and acetic anhydride and dried.

Figure 2:
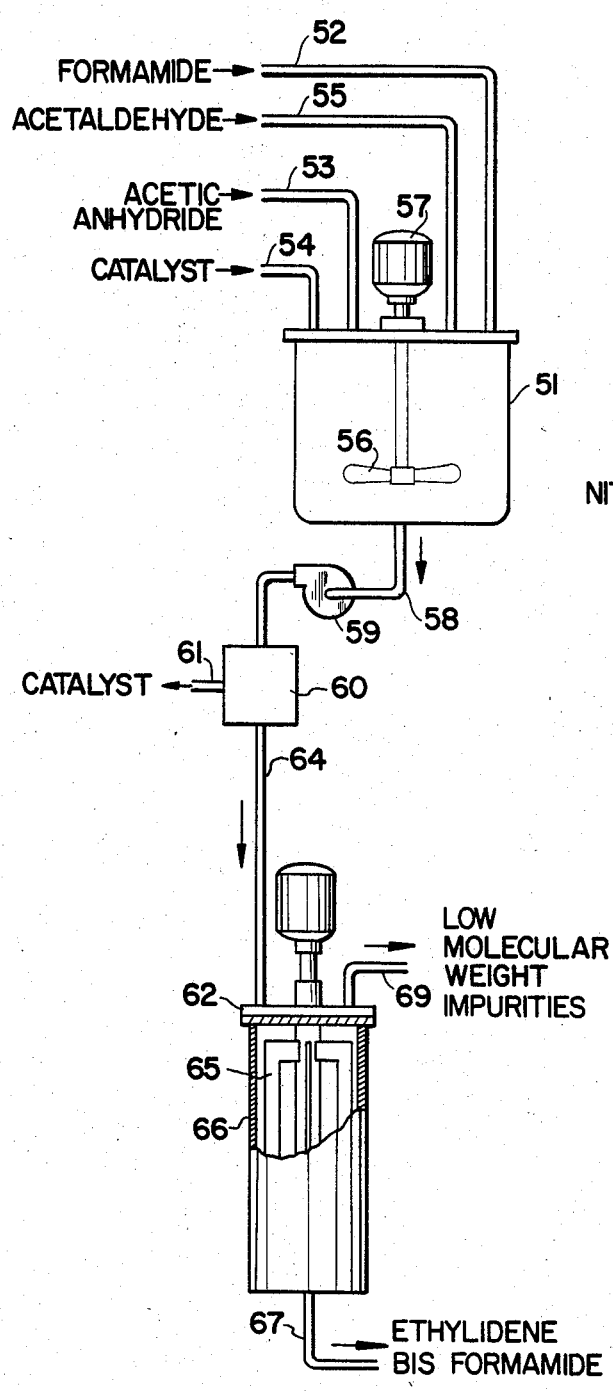
FIG. 2 illustrates a semi-batch embodiment of the invention as it relates to the preparation of ethylidene bisformamide.

In FIG. 2, a schematic flow diagram of a semibatch embodiment of the process of this invention is there depicted. Formamide and acetic anhydride are charged to reactor 51 via conduits 52, and 53 respectively. Particulate ion exchange resin, e.g., sulfonated divinylbenzene-crosslinked polystyrene, is charged to reactor 51 through conduit 54 in an amount of 0.2 kg per 1.0 kg of formamide. Acetaldehyde ($\frac{1}{2}$ to $\frac{1}{3}$ moles per mole of formamide) is then added via conduit 55. The mixture is heated to about 60° C. by means not shown while stirring with agitator 56 driven by electric motor 57. After about 30 minutes, there has been substantial reaction to form ethylidene bisformamide. A crude reaction product comprising water, unreacted acetaldehyde and formamide, acetic acid and ethylidene bisformamide is removed via conduit 58 to metering pump 59 by which it is fed to catalyst filter 60 to form a catalyst phase that is removed via conduit 61 and a catalyst-free stream that is fed to wiped film evaporator 62 by conduit 64. The clearance between the blade 65 and housing 66 of evaporator 62 is such that the surface area of the liquid is about 8-15 cm$^2$/gm. The exposure temperature is about 200° C. and a vacuum in the range of about 25-50 mm Hg absolute is pulled in the evaporator. The ethylidene bisformamide product is withdrawn from the evaporator 62 via conduit 67 to cracking as described in FIG. 1 while the remaining constituents are removed via conduit 69.

The invention will be further described by the following examples. These are provided to illustrate the invention and are not to be construed as limiting in scope.

EXAMPLE I

Condensation

Into a 500 ml round-bottomed flank equipped with overhead stirrer, condenser, pressure regulator, thermowell and oil bath was added 260 g (5.7 moles) of formamide and 10 g of acetic anhydride. These materials were stirred for ten minutes to permit the anhydride to react with any water and ammonia present in the reaction zone. An acidic solid particulate ion exchange catalyst (Bio-Rad AG-MP-50), 70 g, that had been previously washed with a dry solution of acetic anhydride in formamide and then dried, was added. One mole (44 g) of acetaldehyde was then slowly added with stirring. The reaction warmed itself to about 35°-40° C. during 10 minutes. External heat was added until the internal temperature reached 50°-54° C. Seventy minutes after reaction initiation, the reaction mixture was still virtually colorless. An additional ten g of acetic anhydride was then added and the reaction was continued for a total of 2$\frac{1}{2}$ hours. The catalyst was then removed by filtration.

DISTILLATION

A laboratory scale (315 sq cm surface area) wiped film evaporator (WFE) was preheated and turned on. It had a wall temperature profile of from 160° to 210° C. A vacuum was pulled. The bisformamide-containing reaction product was then fed to the WFE at a rate of between 7.75 and 10.6 ml/minute. The WFE vacuum fluctuated as the liquid was fed and averaged about 20-25 mm Hg. absolute. The ethylidene bisformamide was taken off as a pale-yellow clear WFE bottoms in an amount equal to 72% of theoretical. Unreacted formamide and light byproducts were taken off as a vapor phase.

PYROLYSIS

Figure 3:
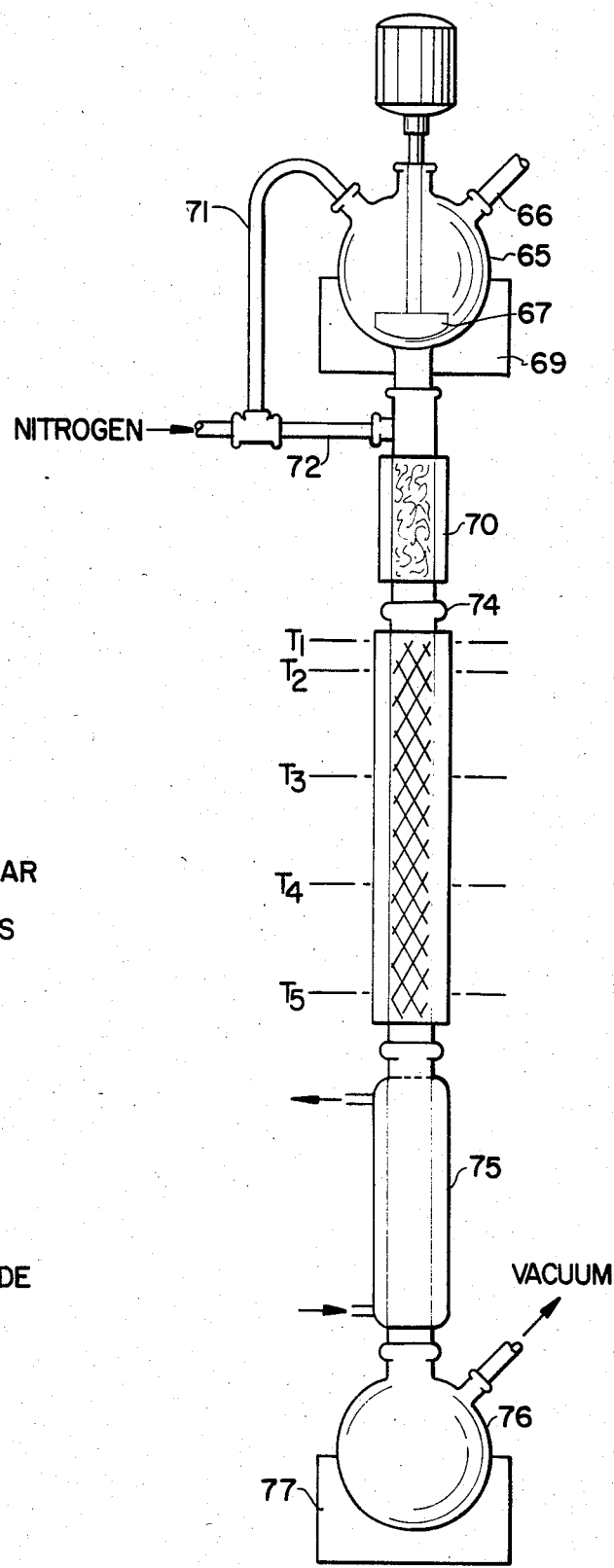
FIG. 3 illustrates a device for pyrolyzing (cracking) ethylidene bisformamide.

The above preparation of this example was repeated several times varying feed concentrations and proportions. The products were the same. One such repeat was pyrolyzed to form N-vinylformamide as follows: An apparatus as shown in FIG. 3 was set up. A 30 g ethylidene bisformamide wiped film evaporator bottoms product was charged to feed pot 65 via line 66. Motor driven agitator 67 and heating bath 69 at 91°-119° C. melted the feed. The melted feed was then poured into evaporator 70 along with a stream of dry nitrogen supplied via line 72. Evaporator 70 was at 252° C. and vaporized the feed. The vaporized feed then passed into pyrolysis tube 74 containing glass helix bed A. The temperature of the bed was monitored at five points, $T_1$, $T_2$, $T_3$, $T_4$, and $T_5$. $T_1$ ranged from 365°-371° C.; $T_2$ 254-266; $T_3$ 369°-454° C.; $T_4$ 543°-541° C. and $T_5$ 577°-607° C. The gaseous pyrolysis product was then condensed in condenser 75 and collected in flask 76 in chiller bath 77. A vacuum of 14-24 mmHg was maintained during the pyrolysis. The liquid product contained formamide, side products, small amounts of unpyrolyzed bisformamide, and N-vinylformamide. While it was not possible to accurately determine a mass balance yield due to losses to equipment, etc., anaylsis indicated a bisformamide conversion of about 95%.

The product was distilled using a lab scale (Bantamware) Vigreaux distillation column. Three cuts were taken with the first being 86-87% N-vinylformamide, the second being 76% N-vinylformamide and the third being 47% N-vinylformamide.

EXAMPLE II

The condensation of Example I was repeated with the following changes:

The reactants were

| Formamide 270 g | 6 moles |
| Acetaldehyde 88 g | 2 moles |
| Acetic Anhydride 4.3 g | 0.04 moles |
| AG-MP-50 Resin 50 g | 0.11 moles |

The resin had been previously rinsed with formamide/acetic anhydride mixture. The condensation was carried out at 51°-67° C. The acetaldehyde was added over a 47 minute period. The total reaction time was 85 minutes. The product was filtered to remove the catalyst. A good quality product, based on its light color, was formed and isolated by WFE.

A twenty gram portion of the product was then pyrolyzed generally following the method of Example I. Two changes were made, however. First, 4 inches of the glass helixes of bed A were replaced with marble chips (CaCO$_3$). Second, the pyrolysis temperature was lowered to 405°-443° C. in the CaCO$_3$ area. Again, 90+% conversions of ethylidene bisformamide to N-vinylformamide were observed.

What is claimed:

1. A process for preparing N-vinylformamide which comprises contacting a liquid admixture comprising formamide, acetaldehyde, and an ammonia scavenger with a catalytic amount of an acidic catalyst at a temperature greater than 50° C. and under conditions sufficient to thereby form an ethylidene bisformamide reaction product, separating said reaction product from the catalyst and recovering from it ethylidene bisformamide using a low residence time-high surface area evaporator, heating the recovered ethylidene bisformamide at a temperature of from 150° to 750° C. in the presence of an inorganic nonacidic surface catalyst for a period of time sufficient to pyrolyze the bisformamide and form a pyrolysis reaction product, and separating N-vinylformamide from the pyrolysis reaction product.

2. The process of claim 1 wherein the catalyst of (i) is glass or marble chips.

3. A process for preparing N-vinylformamide which comprises contacting a substantially water-free liquid admixture comprising formamide, acetaldehyde and acetic anhydride with a catalytic amount of a solid cation exchange resin catalyst for a period of 0.50 hours to 24 hours inclusive at a temperature of from 50° C. to 120° C. thereby forming an ethylidene bisformamide—containing reaction product, separating said reaction product from said catalyst, and recovering the ethylidene bisformamide by using a wiped film evaporator, heating the recovered ethylidene bisformamide at a temperature of 300° to 425° C. and the presence of marble chips for a period sufficient to pyrolyze the ethylidene bisformamide and form an N-vinylformamide-containing reaction product and recovering the N-vinylformamide from said reaction product.

* * * * *